(12) United States Patent
Chasin et al.

(10) Patent No.: US 6,248,746 B1
(45) Date of Patent: Jun. 19, 2001

(54) 3-(ARYLALKYL) XANTHINES

(75) Inventors: Mark Chasin, Manalapan, NJ (US);
David J. Cavalla, Cambridge (GB);
Peter Hofer, Liestal (CH)

(73) Assignee: Euro-Celtique S.A., Petrusse (LU)

( * ) Notice: Subject to any disclaimer, the term of this patent is extended or adjusted under 35 U.S.C. 154(b) by 0 days.

(21) Appl. No.: 09/227,057

(22) Filed: Jan. 7, 1999

Related U.S. Application Data

(60) Provisional application No. 60/070,649, filed on Jan. 7, 1998.

(51) Int. Cl.[7] .................. A61K 31/52; C07D 473/06; C07D 473/04; A61P 11/06; A61P 25/28
(52) U.S. Cl. .................. 514/263; 514/265; 544/267; 544/268; 544/269; 544/210; 544/271; 544/272; 544/273
(58) Field of Search .................. 544/267, 268, 544/269, 220, 271, 272, 273; 514/263, 265

(56) References Cited

U.S. PATENT DOCUMENTS

| | | | |
|---|---|---|---|
| 4,988,689 | 1/1991 | Janssens et al. | 514/212 |
| 5,175,290 | 12/1992 | Rzeszotarski et al. | 544/267 |
| 5,175,291 | 12/1992 | Kufner-Muhl | 544/267 |
| 5,300,298 | 4/1994 | LaNoue | 424/442 |
| 5,334,596 | 8/1994 | Hartman et al. | 514/301 |
| 5,422,350 | 6/1995 | Woolf | 514/252 |
| 5,447,933 | 9/1995 | Suzuki et al. | 514/263 |
| 5,470,579 | 11/1995 | Bonte et al. | 424/450 |

FOREIGN PATENT DOCUMENTS

| | | |
|---|---|---|
| 4707193 | 3/1994 | (AU) . |
| 2091249 | 7/1982 | (GB) . |
| 1156978 | 6/1989 | (JP) . |
| 5105631 | 4/1993 | (JP) . |
| 96/18400 * | 7/1982 | (WO) . |
| WO8805306 | 7/1988 | (WO) . |
| WO9424133 | 10/1994 | (WO) . |
| WO9520589 | 8/1995 | (WO) . |
| WO9748697 | 12/1997 | (WO) . |
| WO9749702 | 12/1997 | (WO) . |

OTHER PUBLICATIONS

Segura, J. Pharm. Pharmacol. 41, 129–131, 1989.*
Merlos, Eur. J Med Chem 25, 653, 1989.*

* cited by examiner

*Primary Examiner*—Mark L. Berch
(74) *Attorney, Agent, or Firm*—Davidson, Davidson & Kappel, LLC

(57) ABSTRACT

With the above and other objects in view, the present invention comprises compounds having the general formula (I):

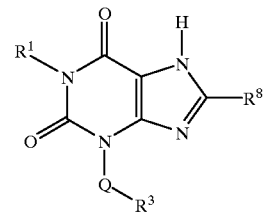

wherein:

$R^1$ is a $C_{2-8}$ alkyl, $C_{2-8}$ alkenyl, $C_{2-8}$ alkynyl, $C_{3-8}$ cycloalkyl, $C_{3-8}$ cycloalkenyl or cycloalkynyl, wherein said alkyl, alkenyl, alkynyl, cycloalkyl, cycloalkenyl or cycloalkynyl is optionally substituted with hydroxy, $C_{1-5}$ alkoxy, $C_{3-5}$ cycloalkoxy, halogen, oxo, carbamido, hydroxycarbamido, oximido, $C_{1-5}$ alkyloximido, $C_{3-5}$ cycloalkyloximido, $C_{1-5}$ acyloximido or $C_{3-5}$ cycloacyloximido;

Q is methylene or ethylene;

$R^3$ is aryl or heteroaryl wherein said aryl or heteroaryl has one to three substituents selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, cycloalkynyl, $C_{3-5}$ alkylene, $C_{3-5}$ cycloalkylene, halo$C_{1-6}$ alkyl, halo$C_{1-6}$ cycloalkyl, hydroxy, $C_{1-5}$ alkoxy, $C_{3-5}$ cycloalkoxy, $C_{1-2}$ alkylenedioxy, $C_{1-6}$ acyl, $C_{3-6}$ cycloacyl, $C_{1-6}$ acyloxy, $C_{3-6}$ cycloacyloxy, halogen, nitro or cyano;

$R^8$ is $C_{1-5}$ alkyl or $C_{3-5}$ cycloalkyl, optionally substituted by hydroxy, $C_{1-5}$ alkyloxy, $C_{3-5}$ cycloalkyloxy, $C_{1-5}$ acyloxy, $C_{3-5}$ cycloacyloxy or halogen;

and methods of using the compounds of formula I for treatment of patients who can benefit from a modification of PDE IV levels in their bodies.

13 Claims, No Drawings

3-(ARYLALKYL) XANTHINES

This application claims the benefit of U.S. Provisional Application No. 60/070,649, filed Jan. 7, 1998.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

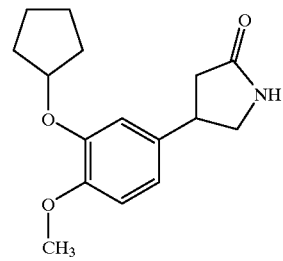

and of RO-20-1724, which has the following structural formula (B):

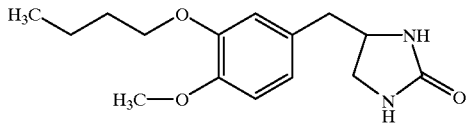

have been studied.

U.S. Pat. No. 4,308,278 discloses compounds of the formula (C)

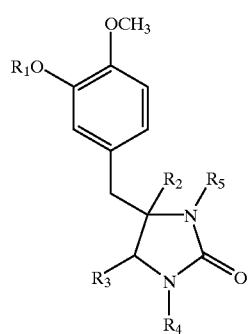

wherein $R_1$ is $(C_3-C_6)$ cycloalkyl or benzyl; each of $R_2$ and $R_3$ is hydrogen or $(C_1-C_4)$ alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

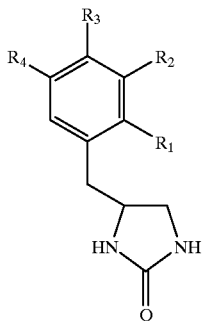

Substituents $R_1$–$R_4$ in Formula D represent a variety of groups, including hydrogen and lower alkyl.

PCT publication WO 87/06576 discloses antidepressants of Formula E:

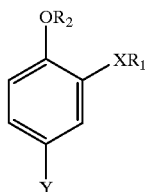

wherein $R_1$ is a polycycloalkyl group having from 7 to 11 carbon atoms; $R_2$ is methyl or ethyl; X is O or NH; and Y comprises of a mono-or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

Additional thioxanthine compounds are known to the art. However, although some have been suggested to be useful for treating, e.g., asthma, the specific anti-PDE IV activity of these compounds has not been determined. For example, French Pharmaceutical Patent No. 835 818 (188M), issued on Aug. 12, 1960 to May & Baker, Ltd. discloses the synthesis of the disubstituted thioxanthines 3-butyl-1-methyl-6-thioxanthine and 3-isobutyl-1-methyl-6-thioxanthine for bronchial or coronary artery dilation without disclosing any PDE IV inhibitory effects. French Pharmaceutical Patent No. 835 811 (188M) also discloses trisubstituted 6-thioxanthines (Formula I) having at the 1 and 3 positions an alcohol or alkyl ($C_{1-6}$), straight or branched and H or an alcohol ($C_{1-6}$) at the 8 position.

Woolridge et al., 1962, J. Chem. Soc. Annex IV:1863–1868 discloses the synthesis of disubstituted 6-thioxanthines: 1,3 and 3,7-disubstituted 6-thioxanthines for bronchial or coronary dilation as well as 1,3,8 lower tri-alkyl substituted 6-thioxanthines where the alkyl groups are methyl or ethyl. PDE IV activity was uncharacterized.

Armitage et al., 1961, Brit. J. Pharm. 17:196–207, disclose trisubstituted 6-thioxanthines having bronchial and coronary dilator activity. The 1,3,8-trisubstituted 6-thioxanthines disclosed by Armitage are 1,3,8-trimethyl-6-thioxanthine and 1,3-dimethyl-8-ethyl-6-thioxanthine.

Some trisubstituted xanthine derivatives having diuretic, renal protective and vasodilator properties are disclosed by U.S. Pat. No. 5,068,236, issued to Suzuki et al. on Nov. 26, 1991. Suzuki et al. disclose xanthines, including trisubstituted xanthines having a lower alkyl independently at positions 1 and 3 and a —$CH_2$—$(R^4)R^5$ group at the 8 position, wherein $R^4$ and $R^5$ are independently substituted or unsubstituted alicyclic alkyl or substituted or unsubstituted aryl. The exemplified trisubstituted compounds having bronchial and coronary dilator activity are not characterized as to PDE IV activity.

Therefore, there remains a continuing need to find new thioxanthine compounds having more selective and improved PDE IV inhibitory activity.

Commonly owned U.S. Pat. No. 4,925,847, issued May 15, 1990, to Hofer, which is hereby incorporated by reference in its entirety, discloses 3,8-alkyl-disubstituted 6-thioxanthines having PDE IV inhibition.

Commonly owned PCT Application No. WO 96/18399, which is hereby incorporated by reference in its entirety, discloses and claims aryl thioxanthines having PDE IV inhibitory activity of formulas I or II, as set forth below:

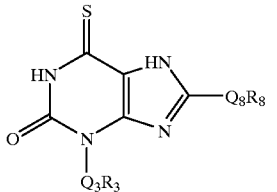

(I)

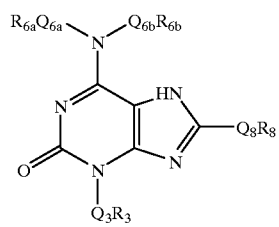

(II)

wherein $Q_3$, $Q_{6a}$, $Q_{6b}$ are independently a bond, $C_{1-8}$ alkylene, $C_{2-8}$ alkenylene and $C_{2-8}$ alkynylene, and $R_3$, $R_{6a}$, $R_{6b}$ and $R_8$ are independently hydrogen, aryl or heteroaryl, optionally substituted by halogen, hydroxy, alkoxy, nitro, cyano and carboxy, provided that $Q_3R_3$ is not hydrogen or methyl in formulas (I) or (II); and at least one of $R^3$ and $R^8$ is aryl or heteroaryl.

Commonly owned PCT Application No. WO 96/18400, which is hereby incorporated by reference in its entirety, discloses and claims Trisubstituted Thioxanthines having PDE IV inhibitory activity of formula I as set forth below:

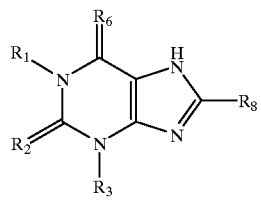

(I)

wherein:

$R_1$, $R_3$ and $R_8$ are independently selected from alkyl, aryl and aralkyl moieties;

$R_2$ and $R_6$ are independently S or O;

with the exception that $R_2$ and $R_6$ are not both O.

It has now been discovered that appropriately substituted 3-(Arylalkyl)Xanthines, which are selected precursors of compounds disclosed in WO 96/18400, show highly increased PDE IV and PDE V inhibitory activity over known xanthine derivatives, including xanthine derivatives described in the aforementioned British Journal of Pharmacology. The compounds of the invention also show increased inhibition of lymphocyte proliferation over the prior art.

OBJECTS AND SUMMARY OF THE INVENTION

It is accordingly a primary object of the present invention to provide new compounds which are more effective selective PDE IV inhibitors.

It is another object of the present invention to provide new compounds which act as effective PDE IV inhibitors with lower PDE III inhibition.

It is a further object of the present invention to provide new compounds which have a superior PDE IV inhibitory effect as compared to theophylline, disubstituted 6-thioxanthines or other known compounds, including known xanthine derivatives.

It is another object of the present invention to provide methods for treating a patient requiring PDE IV inhibition.

It is another object of the present invention to provide new compounds for treating disease states associated with abnormally high physiological levels of cytokines, including tumor necrosis factor.

It is another object of the present invention to provide a method of synthesizing the new compounds of this invention.

It is another object of the present invention to provide a method for treating a patient suffering from disease states such as asthma, allergies, inflammation, depression, dementia, a disease caused by Human Immunodeficiency Virus and disease states associated with abnormally high physiological levels of cytokines.

Other objects and advantages of the present invention will become apparent from the following detailed description thereof.

With the above and other objects in view, the present invention comprises compounds having the general formula (I):

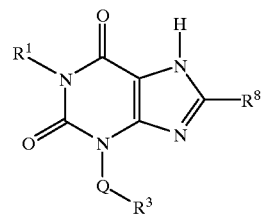

wherein:

$R^1$ is a $C_{2-8}$ alkyl, $C_{2-8}$ alkenyl, $C_{2-8}$ alkynyl, $C_{3-8}$ cycloalkyl, $C_{3-8}$ cycloalkenyl or cycloalkynyl, wherein said alkyl, alkenyl, alkynyl, cycloalkyl, cycloalkenyl or cycloalkynyl is optionally substituted with hydroxy, $C_{1-5}$ alkoxy, $C_{3-5}$ cycloalkoxy, halogen, oxo, carbamido, hydroxycarbamido, oximido, $C_{1-5}$ alkyloximido, $C_{3-5}$ cycloalkyloximido, $C_{1-5}$ acyloximido or $C_{3-5}$ cycloacyloximido;

Q is methylene or ethylene;

$R^3$ is aryl or heteroaryl wherein said aryl or heteroaryl has one to three substituents selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, cycloalkynyl, $C_{3-5}$ alkylene, $C_{3-5}$ cycloalkylene, halo$C_{1-6}$ alkyl, halo$C_{1-6}$ cycloalkyl, hydroxy, $C_{1-5}$ alkoxy, $C_{3-5}$ cycloalkoxy, $C_{1-2}$ alkylenedioxy, $C_{1-6}$ acyl, $C_{3-6}$ cycloacyl, $C_{1-6}$ acyloxy, $C_{3-6}$ cycloacyloxy, halogen, nitro or cyano;

$R^8$ is $C_{1-5}$ alkyl, $C_{2-5}$ alkenyl, $C_{2-5}$ alkynyl, or $C_{3-5}$ cycloalkyl, optionally substituted by hydroxy, $C_{1-5}$ alkoxy, $C_{3-5}$ cycloalkoxy, $C_{1-5}$ acyloxy, benzyloxy, $C_{3-5}$ cycloacyloxy or halogen.

The present invention is also related to methods of using compounds of formula (I) for treating patients who can benefit from a modification of PDE IV levels in their bodies.

Methods of making compounds of formula (I) are also described by the present invention.

The invention is also related to a method of treating mammals with the above compounds.

DETAILED DESCRIPTION OF THE INVENTION

The present invention is directed to compounds having the general formula (I):

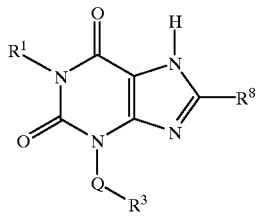

wherein:

R$^1$ is a C$_{2-8}$ alkyl, C$_{2-8}$ alkenyl, C$_{2-8}$ alkynyl, C$_{3-8}$ cycloalkyl, C$_{3-8}$ cycloalkenyl or cycloalkynyl, wherein said alkyl, alkenyl, alkynyl, cycloalkyl, cycloalkenyl or cycloalkynyl is optionally substituted with hydroxy, C$_{1-5}$ alkoxy, C$_{3-5}$ cycloalkoxy, halogen, oxo, carbamido, hydroxycarbamido, oximido, C$_{1-5}$ alkyloximido, C$_{3-5}$ cycloalkyloximido, C$_{1-5}$ acyloximido or C$_{3-5}$ cycloacyloximido;

Q is methylene or ethylene;

R$^3$ is aryl or heteroaryl wherein said aryl or heteroaryl has one to three substituents selected from the group consisting of C$_{1-6}$ alkyl, C$_{2-6}$ alkenyl, C$_{2-6}$ alkynyl, C$_{3-6}$ cycloalkyl, C$_{3-6}$ cycloalkenyl, cycloalkynyl, C$_{3-5}$ alkylene, C$_{3-5}$ cycloalkylene, haloC$_{1-6}$ alkyl, haloC$_{1-6}$ cycloalkyl, hydroxy, C$_{1-5}$ alkoxy, C$_{3-5}$ cycloalkoxy, C$_{1-2}$ alkylenedioxy, C$_{1-6}$ acyl, C$_{3-6}$ cycloacyl, C$_{1-6}$ acyloxy, C$_{3-6}$ cycloacyloxy, halogen, nitro or cyano;

R$^8$ is C$_{1-5}$ alkyl, C$_{2-5}$ alkenyl, C$_{2-5}$ alkynyl, or C$_{3-5}$ cycloalkyl, optionally substituted by hydroxy, C$_{1-5}$ alkyloxy, C$_{3-5}$ cycloalkyloxy, C$_{1-5}$ acyloxy, benzyloxy, C$_{3-5}$ cycloacyloxy or halogen.

The present invention also includes organic and inorganic salts, hydrates, esters, prodrugs and metabolites of the compounds of formula I.

As used herein, the term "patient" includes both human and other mammals.

As used herein, the following terms are intended to have the meaning as understood by persons of ordinary skill in the art, and are specifically intended to include the meanings set forth below:

"Hydro" means a single hydrogen atom.

"Alkyl", whether used alone or as part of another group such as "haloalkyl" or arylalkyl", means a linear or branched aliphatic hydrocarbon group having a single radical. Examples of alkyl groups include methyl, propyl, isopropyl, butyl, n-butyl, isobutyl, sec-butyl, tert-butyl, pentyl, hexyl, heptyl, cetyl, and the like. The term "lower alkyl" means a linear or branched hydrocarbon group having from one to about 12 carbon atoms, and having a single radical. A branched alkyl means that one or more lower alkyl groups such as methyl, ethyl or propyl are attached to a linear alkyl chain.

The term "haloalkyl" embraces radicals wherein any one or more of the alkyl carbon atoms is substituted with a halogen. Examples of haloalkyl radicals include fluoromethyl, difluoromethyl, trifluoromethyl, chloromethyl, dichloromethyl and trichloromethyl.

The term "hydroxyalkyl" embraces radicals wherein any one or more of the alkyl carbon atoms is substituted with a hydroxy. Examples of hydroxyalkyl radicals include hydroxymethyl, hydroxyethyl, hydroxybutyl, hydroxypropyl.

The term "cycloalkyl" means a non-aromatic mono- or multicyclic ring system of about 3 to about 10 carbon atoms having a single radical. Preferred monocyclic cycloalkyl rings include cyclopentyl, cyclohexyl and cycloheptyl. Exemplary multicylic cycloalkyl rings include 1-decalin, adamant-(1-or2-)yl and norbornyl.

The term "cycloalkylalkyl" or "cycloalkyl-alkyl" means a non-aromatic mono- or multicyclic ring system of about 3 to about 10 carbon atoms, wherein the ring is substituted with an alkyl group, as defined above to include a linear or branched aliphatic hydrocarbon group having a single radical.

As used herein, the term "alkenyl" means an aliphatic hydrocarbon group having a single radical and containing a carbon-carbon double bond and which may be straight or branched having about 2 to about 15 carbon atoms in the chain. A "branched" alkenyl means that one or more lower alkyl groups such as methyl, ethyl or propyl are attached to a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl and decenyl.

The term "cycloalkenyl" means a non-aromatic monocyclic or multicyclic ring system having a single radical and containing a carbon-carbon double bond and having about 3 to about 10 carbon atoms. Exemplary monocyclic cycloalkenyl rings include cyclopentenyl, cyclohexenyl or cycloheptenyl. An exemplary multicyclic cycloalkenyl ring is norbornenyl.

The term "alkynyl" means an aliphatic hydrocarbon group having a single radical and containing a carbon-carbon triple bond and which may be straight or branched having about 2 to about 15 carbon atoms in the chain. A "branched" alkynyl means that one or more lower alkyl groups such as methyl, ethyl or propyl are attached to a linear alkynyl chain. "Lower alkynyl" means an alkynyl group having about 2 to about 4 carbon atoms in the chain which may be straight or branched.

The term "cycloalkynyl" means a non-aromatic monocyclic or multicyclic ring system having a single radical and containing a carbon-carbon triple bond and having about 3 to about 10 carbon atoms. An exemplary monocyclic cycloalkynyl ring is cyclooctynyl.

The term "alkylene" means a linear or branched aliphatic hydrocarbon group having two radicals. Exemplary alkylene groups are methylene and ethylene.

The term "alkenylene" means a linear or branched aliphatic hydrocarbon group having at least one carbon-carbon double bond and two radicals.

The term "alkynylene" means a linear or branched aliphatic hydrocarbon group having a single carbon-carbon triple bond and two radicals.

The term "aryl" means an aromatic carbocyclic radical having a single radical and containing 6 or 10 resonance electrons. Exemplary aryl groups include phenyl and naphthyl.

The term "arylene" means an aromatic carbocyclic radical having two radicals and containing 6 or 10 resonance electrons. Exemplary arylene groups include phenylene and naphthylene.

The term "aralkyl" or "arylalkyl" or "aryl-alkyl" means an aryl group as defined above which is substituted with a linear or branched aliphatic hydrocarbon group.

The term "heteroaryl" or "heteroaromatic" or "heterocyclic aromatic" means a 5- to 10-membered aromatic monocyclic or multicyclic ring system having a single radical and containing at least one carbon atom in the ring and containing 6 or 10 resonance electrons in which one or more of the ring atoms is/are element(s) other than carbon, for example nitrogen, oxygen or sulfur. Exemplary heteroaryl groups include pyrazinyl, furanyl, thienyl, pyridyl, pyrimidinyl, isoxazolyl, isothiazolyl, quinolinyl, and isoquinolinyl.

The term "heteroaralkyl" or "heteroaryl-alkyl" means a heteroaryl group as defined above to include a 5- to 10-membered aromatic monocyclic or multicyclic ring system containing at least one carbon atom in the ring and containing 6 or 10 resonance electrons in which one or more of the ring atoms is/are element(s) other than carbon, for example nitrogen, oxygen or sulfur, in which the heteroaryl group is substituted with an alkyl group as defined above to include a linear or branched aliphatic hydrocarbon group.

The term "heterocyclic" means cyclic compounds having a single radical and containing one or more atoms other than carbon in the ring. The ring may be saturated, partially saturated and unsaturated heteroatom-containing radicals, where the heteroatoms may be selected from nitrogen, sulfur and oxygen. Examples of saturated heterocyclic radicals include saturated 3 to 6-membered heteromonocyclic groups containing 1 to 4 nitrogen atoms, such as pyrrolidinyl, imidazolidinyl, piperidino, piperazinyl; saturated 3- to 6-membered heteromonocyclic groups containing 1 to 2 oxygen atoms and 1 to 3 nitrogen atoms, such as thiazolidinyl. Examples of partially saturated heterocyclic radicals include dihydrothiophene, dihydropyran, dihydrofuran.

"Acyl" means an H—CO- or alkyl- CO- group in which the alkyl group is as previously defined above. Exemplary acyl groups include formyl, acetyl, propanoyl, 2-methylpropanoyl, butanoyl and palmitoyl. "Cycloacyl" means an H- CO- or cycloalkyl- CO- group in which the cycloalkyl group is as previously defined above.

"Acyloxy" means an acyl- O- group in which the acyl group is as previously defined. The term "cycloacyloxy" means a cycloacyl- O- group in which the cycloacyl group is as previously defined above.

"Alkoxy" means an alkyl- O- group in which the alkyl group is as previously defined. Exemplary alkoxy groups include methoxy, ethoxy, n-propoxy, i-propoxy, n-butoxy and heptoxy. The term "cycloalkoxy" means a cycloalkyl- O- group in which the cycloalkyl group is as previously defined above. Exemplary cycloalkoxy groups include cyclopentyloxy.

"Alkylenedioxy" means an $R^9$—O—alkylene- O— $R^{10}$ group in which the alkylene is as defined above, and $R^9$ and $R^{10}$ are selected from the group consisting of an alkyl, alkenyl, alkynyl, cycloalkyl, cycloalkenyl, cycloalkynyl, aryl, heteroaryl, heterocyclic, or $R^9$ and $R^{10}$ together is a single alkylene, alkenylyene, alkynylene, cycloalkylene, cycloalkenylyene, cycloalkynylene or arylene group. Exemplary alkylenedioxy groups are $C_{1-2}$ alkylenedioxy wherein the $C_{1-2}$ refers to the length of the alkylene chain. Exemplary $C_{1-2}$ alkylenedioxy groups are depicted below:

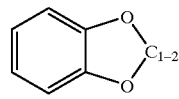

The term "amido" or "aminocarbonyl" means —C(O)NH$_2$, as depicted below:

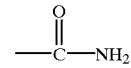

The term "amino" means the group —NH$_2$—.
The term "carbamido" or "(aminocarbonyl)amino" is the group having the formula H$_2$NCONH—, as depicted below:

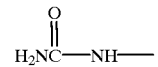

The term "carbamyl" is the group NH$_2$CO, as depicted below:

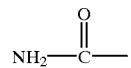

The term "carboxy" or "carboxyl", whether used alone or in combination with other groups, such as "carboxyalkyl", denotes —CO$_2$H, as depicted below:

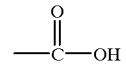

The term "carboxamido" means —NHC(O)—, as depicted below:

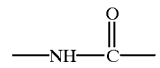

The term "carbonyl", whether used alone or in combination with other terms, such as "alkoxycarbonyl", denotes —(C=O)—. The term "alkoxycarbonyl" means a radical containing an alkoxy radical, as defined above, attached via an oxygen atom to a carbonyl radical.

The term "cyano", whether used alone or in combination with other terms, such as "cyanoalkyl", denotes —C≡N—.

The term "oximido" or "hydroxyimino" means the group HO—N=.

The term "oxo" means O=.

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solutions and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agent, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients,* American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems,* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions or emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

Compounds falling into the genus of PDE IV inhibitors of the present invention include:

3-(4-Chlorobenzyl)-1-ethyl-8-isopropyl-xanthine;

3-(3-cyclopentyloxy-4-methoxy-benzyl)1-ethyl-8-isopropyl-xanthine;

3-(3,4-dimethoxybenzyl)-1-ethyl-8-isopropyl-xanthine; and 1-ethyl-8-isopropyl-3-(3,4-methylenedioxybenzyl)-xanthine.

DETAILED DESCRIPTION OF PREFERRED EMBODIMENTS

The following examples illustrate various aspects of the present invention:

EXAMPLE 1

3-(3,4-dimethoxybenzyl)-1-ethyl-8-isopropyl-xanthine a) (3,4-Dimethoxybenzyl)urea 60 ml of 5n HCl were added at room temperature within 45 min to a solution of 49.5 ml (300 mM) of 90% veratrylamine and 20.40 g (307 mM) of 98% sodium cyanate in 500 ml of water. After stirring overnight the crystals were collected: 52.66 g (83.5%) of urea with a melting point of 172–3° C. (sublimation 157° C.).

b) 1-Cyanoacetyl-3-(3,4-dimethoxybenzyl)-urea 25.89 g (298 mM) of 98% cyanoacetic acid and 101.9 ml of acetic anhydride were kept for 1 hour at 65° C. with stirring. A suspension of 59.70 g (284 mM) of (3,4-dimethoxybenzyl)urea in 600 ml of THF was added with an additional 250 ml of THF. After 10 minutes at reflux a solution is formed, which is kept at reflux for 6 hrs. After over night stirring at room temperature the formed crystals were collected: 64.82 g (82.3%) of the title urea with a melting point of 187–8° C.

c) 6-Amino-1-(3,4-dimethoxybenzyl)-uracil

A suspension of 68.21 g (246 mM) of the above urea in 900 ml of isopropanol was added with an additional 200 ml of isopropanol to a solution of 3.45 g (61.5 mM) of KOH in 180 ml of isopropanol. During heating to reflux an exothermic reaction ocurred. After 50 minutes at reflux the suspension was cooled to −5° C. and the solid collected: 54.50 g (79.9%) of uracil hydrate with a melting point of 254–6° C. (sublimation 237° C.). The motherliquor gave from neutral water an additional 11.53 g (16.9%) of uracil.

d) 6-Amino-1-(3,4-dimethoxybenzyl)-5-nitroso-uracil 56.1 ml of 4N sodium nitrite solution was added at 65–70° C. to a suspension of 61.0 g (220 mM) of uracil in 1200 ml of acetic acid within 15 minutes. After about 50% addition an intermediate solution was formed. After a further 45 minutes the newly formed suspension was cooled to room temperature and the solid collected, dissolved in 500 ml of 1N NaOH, the solution acidified with 80 ml of 5N HCl to pH 6.5 and the solid once more collected: 56.69 g (79.5%) of nitrosouracil hydrate with a melting point starting at 235° C. (decomposition).

e) 6-Amino-1-(3,4-dimethoxybenzyl)-5-isobutyrylamino-uracil 57.45 g (280 mM) of 85% sodium dithionate was added in portions to a suspension of 60.4 g (187 mM) of nitrosouracil and 6.3 ml of 85% phosphoric acid in 600 ml of THF and 220 ml of water. After 40 minutes an additional 19.15 g (94 mM) of sodium dithionate was added. After 15 minutes 40.6 ml (280 mM) of isobutyric anhydride was added and the mixture stirred over night. The THF was removed in vacuo and replaced by water. The suspension was brought to pH 7.5 with 2n NaOH and the solid collected: 59.84 g (84.1%) of isobutyrylaminouracil with a melting point of 207–10° C.

f) 3-(3,4-dimethoxybenzyl)-1-ethyl-8-isopropyl-xanthine

At 0–5° C. 3.54 g of t-BuOK were added to a water free solution of 11.41 g (30 mM) of isobutyrylaminouracil hydrate in 125 ml of DMF followed by 2.46 ml of ethylbromide. After 3 hours at 0–5° C. a further 0.89 g of t-BuOK and 1.23 ml of ethylbromide were added. After stirring overnight at room temperature the solution was acidified to pH 6 with 1N HCl and the DMF removed in vacuo. The gummy material was extracted with ethyl acetate and evaporated to dryness. The residue was refluxed in 130 ml of 1N NaOH for 1 hour, treated with 1.0 g of char coal, filtered and neutralized with 2N HCl. The solid is collected and crystallized from methanol: 6.16 g (55.2%) of title xanthine with a melting point of 198–201° C.

Elemental analysis for $C_{19}H_{24}N_4O_4/372.42$

| % calc  | C 61.28 | H 6.50 | N 15.04 | O 17.18 |
|---------|---------|--------|---------|---------|
| % found | C 61.19 | H 6.61 | N 15.15 | O 17.29 |

EXAMPLE 2

1-Ethyl-8-isopropyl-3-(3,4-methylenedioxybenzyl)-xanthine a) (3,4-Methylenedioxybenzyl)urea 61.5 ml of 5N HCl was added within 30 minutes to a stirred emulsion of 38.51 ml (300 mM) of 97% piperonylamine and 20.40 g of sodium cyanate in 500 ml of water. After stirring overnight the foamy solid is collected, dried, suspended in 500 ml of ether and collected again: 52.57 g (90.2%) of urea with a melting point of 183–84° C.

b) 1-Cyanoacetyl-3-(3,4-methylenedioxybenzyl-urea 24.62 g (283.5 mM) of cyanoacetic acid 98% and 97 ml of acetic anhydride were kept for 1 hour at 65° C. At 50° C. a suspension of 52.41 g (270 mM) of (3,4-methylenedioxybenzyl)urea in 600 ml of THF was added and the mixture refluxed for 8 hours. After cooling to 5° C. the solid was collected and washed with a mixture of 1 part of THF and 3 parts of ether and ether: 56.90 g (80.7%) of the title urea with mp 183–4° C. The filtrate was concentrated in vacuo, the residue suspended in water and neutralized with 2N NaOH to pH 7.5. The solid was collected as a second batch: 11.66 g (16.5%, total 97.2%).

c) 4-Amino-3-(3,4-methylenedioxybenzyl)-uracil

A suspension of 68.44 g (262 mM) of cyanoacetylurea in 1300 ml of isopropanol was added to a solution of 3.67 g (65.5 mM) of KOH in 180 ml of isopropanol and the mixture refluxed for 1 hour. After cooling to 5° C. the solid was collected and washed with cold isopropanol: 54.13 g (79.1%) of the title uracil with melting point of 283–91 ° C. The filtrate was evaporated to dryness, the residue suspended in water, with 4.5 ml of 5n HCl neutralized to pH 7, and the solid collected at 5° C.: 13.53 g (19.8%, total 98.9%).

d) 4-Amino-5-isobutyramido-3-(3,4-methylenedioxybenzyl)-uracil 26.25 ml (105 mM) of 4n sodium nitrite was added within 15 minutes at 55–60° C. to a suspension of 26.12 g (100 mM) of the above uracil and 7.45 ml (110 mM) of 85% phosphoric acid in 500 ml of THF. After 30 minutes the pink suspension was cooled to 35° C. and a suspension of 40.95 g (200 mM) of 85% sodium dithionite in 80 ml of water added. After 2 hours at 40° C. another 8 g (40 mM) in 40 ml of water were added. After a further 30 minutes the mixture was cooled to 25° C. and treated with 24.90 ml (150 mM) of isobutyric anhydride, the mixture refluxed for 1 hour and stirred overnight at room temperature. The THF was removed in vacuo, the residue diluted with 250 ml of water and neutralized with 300 ml of 2n NaOH to pH 7, cooled to 5° C., and the solid was collected. It still contained the diaminouracil intermediate. Thereafter the crude product was suspended in 400 ml of THF, treated with 8.3 ml (50 mM) of isobutyric anhydride, and refluxed again for 1 hour. The THF was removed in vacuo, the residue treated with 200 ml of water, and the remaining THF removed in vacuo. The suspension was neutralized with 2n NaOH to pH 7.5 and the solid collected: 26.97 g (77.9%) of crude isobutyramidouracil with a melting point of 233–43° C. A sample crystallized from methanol had a melting point of 249–50° C.

e) 4-Amino-1-ethyl-5-isobutyramido-3-(3,4-methylenedioxybenzyl)-uracil 0.80 g (7.14 mM) of potassium t-butylate followed by 0.58 ml (7.70 mM) of bromoethane were added at 0–3° C. to a solution of 2.42 g (7.00 mM) of the above uracil in 30 ml of DMF. After 3 hours another 0.2 g of butylate and 0.29 ml of bromoethane were added. After 5 hours at 0–3° C. the mixture was allowed to reach room temperature overnight. The solution was neutralized with about 1 ml of 1n HCl to pH 6.5–7.0 and the DMF removed in vacuo. The crystalline residue is suspended in water and the solid collected at 5° C.: 2.03 g (77.5%) of 1-ethyluracil.

f) 1-Ethyl-8-isopropyl-3-(3,4-methylenedioxybenzyl)-xanthine

A suspension of 1.87 g (5 mM) of 1-ethyluracil in 30 ml of 1n NaOH were refluxed for 1 hour (formation of solution), treated twice with 0.1 g of charcoal, filtered, and acidified with 6 ml of 5n HCl to pH 5.5. The solid was collected: 1.37 g (77.0%) of xanthine with a melting point of 200°–232° C.

Elemental analysis for $C_{18}H_{20}N_4O_4/356.38$

| % calc  | C 60.66 | H 5.66 | N 15.72 | O 17.96 |
|---------|---------|--------|---------|---------|
| % found | C 60.44 | H 5.77 | N 15.68 | O 18.13 |

While the invention has been illustrated with respect to the production and use of particular compounds, it is apparent that variations and modifications of the invention can be made without departing from the spirit or scope of the invention.

What is claimed is:

1. A compound having the formula (I):

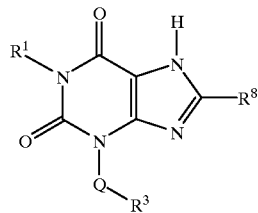

wherein $R_1$ is a $C_{2-8}$ alkyl, $C_{2-8}$ alkenyl, $C_{2-8}$ alkynyl, $C_{3-8}$ cycloalkyl, $C_{3-8}$ cycloalkenyl or cycloalkynyl, wherein said alkyl, alkenyl, alkynyl, cycloalkyl, cycloalkenyl or cycloalkynyl is optionally substituted with hydroxy, $C_{1-5}$ alkoxy, $C_{3-5}$ cycloalkoxy, halogen, oxo, carbamido, hydroxycarbamido, oximido, $C_{1-5}$ alkyloximido, $C_{3-5}$ cycloalkyloximido, $C_{1-5}$ acyloximido or $C_{3-5}$ cycloacyloximido;

Q is methylene or ethylene;

$R_3$ is aryl or heteroaryl wherein said aryl or heteroaryl has one to three substituents selected from the group consisting of $C_{2-6}$ alkyl, $C_{2-6}$ alkenyl, $C_{2-6}$ alkynyl, $C_{3-6}$ cycloalkyl, $C_{3-6}$ cycloalkenyl, cycloalkynyl, $C_{3-5}$ alkylene, $C_{3-5}$ cycloalkylene, halo$C_{1-6}$ alkyl, halo$C_{1-6}$ cycloalkyl, $C_{3-5}$ cycloalkoxy, $C_{1-2}$ alkylenedioxy, $C_{1-6}$ acyl, $C_3$–$C_{10}$ cycloacyl, $C_{1-6}$ acyloxy, .$C_{3-6}$ cycloacyloxy, nitro or cyano;

$R_8$ is $C_{1-5}$ alkyl, $C_{2-5}$ alkenyl, $C_{2-5}$ alkynyl, or $C_{3-5}$ cycloalkyl optionally substituted by hydroxy, $C_{1-5}$ alkyloxy, $C_{3-5}$ cycloalkyloxy, $C_{1-5}$ acyloxy, benzyloxy, $C_{3-5}$ cycloacyloxy or halogen.

2. A compound of claim 1 which is 1-ethyl-8-isopropyl-3-(3,4-methylenedioxybenzyl)-xanthine.

3. A pharmaceutical composition comprising a compound of claim 1 and a pharmaceutically acceptable carrier or excipient.

4. A method of effecting PDE-IV inhibition for treating human patients suffering from a disease state selected from the group consisting of asthma, allergies, atopic diseases and rhinitis, comprising administering an effective amount of a compound having the formula (I):

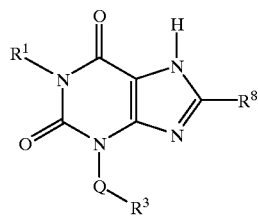

wherein $R_1$ is a $C_{2-8}$ alkyl, $C_{2-8}$ alkenyl, $C_{2-8}$ alkynyl, $C_{3-8}$ cycloalky, $C_{3-8}$ cycloalkenyl or cycloalkynyl, wherein said alkyl, alkenyl, alkynyl, cycloalkyl, cycloalkenyl or cycloalkynyl is optionally substituted with hydroxy, $C_{1-5}$ alkoxy, $C_{3-5}$ cycloalkoxy, halogen, oxo, hydroxycarbamido, oximido, $C_{1-5}$ alkyloximido, $C_{3-5}$ cycloalkyloximido, $C_{1-5}$ acyloximido or $C_{3-5}$ cycloacyloximido;

Q is methylene or ethylene;

$R_3$ is aryl or heteroaryl wherein said aryl or heteroaryl has one to three substituents selected from the group consisting of $C_{2-6}$ alkyl, $C_{2-6}$ alkenyl, $C_{2-6}$ alkynyl, $C_{3-6}$ cycloalkyl, $C_{3-6}$ cycloalkenyl, cycloalkynyl, $C_{3-5}$ alkylene, $C_{3-5}$ cycloalkylene, halo$C_{1-6}$ alkyl, halo$C_{1-6}$ cycloalkyl, hydroxy, $C_{1-5}$ alkoxy, $C_{1-2}$ alkylenedioxy, $C_{1-6}$ acyl, $C_3$–$C_{10}$ cycloacyl, $C_{1-6}$ acyloxy, $C_{3-6}$ cycloacyloxy, halogen, nitro or cyano;

$R_8$ is $C_{1-5}$ alkyl, $C_{2-5}$ alkenyl, $C_{2-5}$ alkynyl, or $C_{3-5}$ cycloalkyl optionally substituted by hydroxy, $C_{1-5}$ alkyloxy, $C_{3-5}$ cycloalkyloxy, $C_{1-5}$ acyloxy, benzyloxy, $C_{3-5}$ cycloacyloxy or halogen.

5. The method of claim 4 wherein said compound is 3-(3,4-dimethoxybenzyl)-1-ethyl-8-isopropyl-xanthine.

6. A pharmaceutical composition as defined in claim 3, wherein the pharmaceutical acceptable carrier or excipient is selected from the group consisting of diluents, suspending agents, solubilizers, binders, disintegrants, preservatives, coloring agents, lubricants and combinations thereof.

7. A method of effecting PDE-IV inhibition in a human patient suffering from asthma, allergies, atopic diseases and rhinitis, comprising administering an effective amount of a compound of claim 1.

8. A compound having the formula (I):

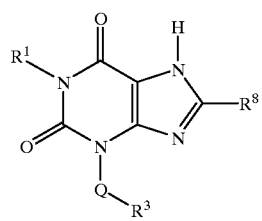

wherein $R_1$ is a $C_{3-8}$ cycloalkenyl or cycloalkynyl, wherein said cycloalkenyl or cycloalkynyl is optionally substituted with hydroxy, $C_{1-5}$ alkoxy, $C_{3-5}$ cycloalkoxy, halogen, oxo, carbamido, hydroxycarbamido, oximido, $C_{1-5}$ alkyloximido, $C_{3-5}$ cycloalkyloximido, $C_{1-5}$ acyloximido or $C_{3-5}$ cycloacyloximido;

Q is methylene or ethylene;

$R_3$ is aryl or heteroaryl wherein said aryl or heteroaryl has one to three substituents selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, cycloalkynyl, $C_{3-5}$ alkylene, $C_{3-5}$ cycloalkylene, halo$C_{1-6}$ alkyl, halo$C_{1-6}$ cycloalkyl, hydroxy, $C_{1-5}$ alkoxy, $C_{3-5}$ cycloalkoxy, $C_{1-2}$ alkylenedioxy, $C_{1-6}$ acyl, $C_3$–$C_{10}$ cycloacyl, $C_{1-6}$ acyloxy, $C_{3-6}$ cycloacyloxy, halogen, nitro or cyano;

$R_8$ is $C_{1-5}$ alkyl, $C_{2-5}$ alkenyl, $C_{2-5}$ alkynyl, or $C_{3-5}$ cycloalkyl optionally substituted by hydroxy, $C_{1-5}$ alkyloxy, $C_{3-5}$ cycloalkyloxy, $C_{1-5}$ acyloxy, benzyloxy, $C_{3-5}$ cycloacyloxy or halogen.

9. A method of effecting PDE-IV inhibition in a human patient suffering from asthma, allergies, atopic diseases and rhinitis, comprising administering an effective amount of a compound of claim 8.

10. A pharmaceutical composition comprising a compound of claim 8 and a pharmaceutical acceptable carrier or excipient.

11. A compound having the formula (I):

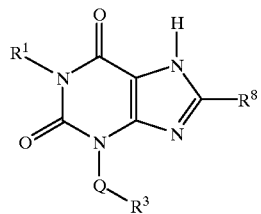

wherein $R_1$ is a $C_{2-8}$ alkyl, $C_{2-8}$ alkenyl, $C_{2-8}$ alkynyl, $C_{3-8}$ cycloalky, $C_{3-8}$ cycloalkenyl or cycloalkynyl, wherein said alkyl, alkenyl, alkynyl, cycloalkyl, cycloalkenyl or cycloalkynyl is optionally substituted with hydroxy, $C_{1-5}$ alkoxy, $C_{3-5}$ cycloalkoxy, halogen, oxo, carbamido, hydroxycarbamido, oximido, $C_{1-5}$ alkyloximido, $C_{3-5}$ cycloalkyloximido, $C_{1-5}$ acyloximido or $C_{3-5}$ cycloacyloximido;

Q is methylene or ethylene;

$R_3$ is aryl or heteroaryl wherein said aryl or heteroaryl has one to three substituents selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, cycloalkynyl, $C_{3-5}$ alkylene, $C_{3-5}$ cycloalkylene, halo$C_{1-6}$ alkyl, halo$C_{1-6}$ cycloalkyl, hydroxy, $C_{1-5}$ alkoxy, $C_{3-5}$ cycloalkoxy, $C_{1-2}$ alkylenedioxy, $C_{1-6}$ acyl, $C_3$–$C_{10}$ cycloacyl, $C_{1-6}$ acyloxy, $C_{3-6}$ cycloacyloxy, halogen, nitro or cyano;

$R_8$ is $C_{2-5}$ alkenyl or $C_{2-5}$ alkynyl, optionally substituted by hydroxy, $C_{1-5}$ alkyloxy, $C_{3-5}$ cycloalkyloxy, $C_{1-5}$ acyloxy, benzyloxy, $C_{3-5}$ cycloacyloxy or halogen.

12. A method of effecting PDE-IV inhibition for treating human patients suffering from a disease state selected from the group consisting of asthma, allergies, atopic diseases and rhinitis, comprising administering an effective amount of a compound of claim 11.

13. A pharmaceutical composition comprising a compound of claim 11 and a pharmaceutical acceptable carrier or excipient.

* * * * *